(12) United States Patent
Halim et al.

(10) Patent No.: US 9,430,734 B2
(45) Date of Patent: Aug. 30, 2016

(54) METHOD AND SYSTEM FOR VALIDATING ENERGY MEASUREMENT IN A HIGH PRESSURE GAS DISTRIBUTION NETWORK

(75) Inventors: M. Huzainy B. Halim, Tronoh Perak (MY); Rosdiazli Ibrahim, Tronoh Perak (MY); Idris Ismail, Tronoh Perak (MY); Maryam Jamela Ismail, Tronoh Perak (MY)

(73) Assignee: PETROLIAM NASIONAL BARHAD (PETRONAS), Kuala Lumpur (MY)

( * ) Notice: Subject to any disclaimer, the term of this patent is extended or adjusted under 35 U.S.C. 154(b) by 917 days.

(21) Appl. No.: 13/806,970

(22) PCT Filed: Apr. 29, 2011

(86) PCT No.: PCT/MY2011/000039
§ 371 (c)(1),
(2), (4) Date: Jul. 31, 2014

(87) PCT Pub. No.: WO2011/162592
PCT Pub. Date: Dec. 29, 2011

(65) Prior Publication Data
US 2014/0351187 A1 Nov. 27, 2014

(30) Foreign Application Priority Data
Jun. 25, 2010 (MY) .............................. 2010003059

(51) Int. Cl.
*G06F 15/18* (2006.01)
*G06E 1/00* (2006.01)
*G06E 3/00* (2006.01)
(Continued)

(52) U.S. Cl.
CPC *G06N 3/02* (2013.01); *G01K 17/00* (2013.01); *G01N 33/225* (2013.01)

(58) Field of Classification Search
CPC combination set(s) only.
See application file for complete search history.

(56) References Cited

U.S. PATENT DOCUMENTS 5,180,911 A 1/1993 Grossman et al.
5,729,623 A 3/1998 Omatu et al.
(Continued)

FOREIGN PATENT DOCUMENTS

CN 1184931 A 6/1998
CN 1595323 A 3/2005
(Continued)

OTHER PUBLICATIONS

Cavitation Regime Detection by LS-SVM and ANN With Wavelet Decomposition Based on Pressure Sensor Signals Maria Grazia De Giorgi; Antonio Ficarella; Aimé Lay-Ekuakille IEEE Sensors Journal Year: 2015, vol. 15, Issue: 10 pp. 5701-5708, DOI: 10.1109/JSEN.2015.2447518 IEEE Journals & Magazines.*
(Continued)

*Primary Examiner* — Michael B Holmes
(74) *Attorney, Agent, or Firm* — Marshall, Gerstein & Borun LLP

(57) ABSTRACT

A method and system for validating energy measurement in a high pressure gas distribution network. The method comprises the steps of calculating a validation energy value using an artificial neural network (ANN) engine based on measured parameters associated with a gas flow in the gas distribution network; measuring an actual energy value of the gas flow; and comparing the validation energy value and the actual energy value, wherein the actual energy value is validated if the validation energy value and the actual energy value are substantially equal.

21 Claims, 13 Drawing Sheets

(51) Int. Cl.
*G06G 7/00* (2006.01)
*G06N 3/02* (2006.01)
*G01K 17/00* (2006.01)
*G01N 33/22* (2006.01)

(56) References Cited

U.S. PATENT DOCUMENTS

| | | | |
|---|---|---|---|
| 6,119,529 | A | 9/2000 | Di Marco et al. |
| 6,192,352 | B1 | 2/2001 | Alouani et al. |
| 6,567,795 | B2 | 5/2003 | Alouani et al. |
| 6,598,459 | B1 | 7/2003 | Fu |
| 8,709,551 | B2* | 4/2014 | Fox ............... H01L 21/0214 427/248.1 |
| 8,741,394 | B2* | 6/2014 | Haverkamp ............ C23C 16/24 427/534 |
| 8,756,928 | B2* | 6/2014 | Fong ............... F01K 25/06 60/370 |
| 8,769,943 | B2* | 7/2014 | Fong ............... F01K 25/06 60/370 |
| 8,844,277 | B2* | 9/2014 | Fong ............... F01K 25/06 60/370 |
| 8,893,486 | B2* | 11/2014 | Fong ............... F01K 25/06 60/370 |
| 8,893,487 | B2* | 11/2014 | Fong ............... F01K 25/06 60/370 |
| 8,895,415 | B1* | 11/2014 | Fox ............... H01L 21/02532 438/482 |
| 8,912,684 | B2* | 12/2014 | Stahlkopf ............ F01K 13/02 307/87 |
| 8,919,112 | B1* | 12/2014 | Fong ............... F01K 25/06 60/398 |
| 9,117,668 | B2* | 8/2015 | Hollister ............ H01L 21/0245 |
| 9,298,197 | B2* | 3/2016 | Matsuoka ............ G05D 23/1917 |
| 9,382,799 | * | 7/2016 | Stahlkopf ............ F01B 17/02 |
| 2001/0001149 | A1 | 5/2001 | Alouani et al. |
| 2002/0059154 | A1 | 5/2002 | Rodvold |
| 2004/0016287 | A1 | 1/2004 | Fu |
| 2004/0213448 | A1 | 10/2004 | Jou et al. |
| 2008/0306892 | A1 | 12/2008 | Crossley et al. |

FOREIGN PATENT DOCUMENTS

| | | |
|---|---|---|
| CN | 1661004 A | 8/2005 |
| CN | 1996192 A | 7/2007 |
| CN | 101030258 A | 9/2007 |
| CN | 101127160 A | 2/2008 |
| CN | 101187660 A | 5/2008 |
| CN | 101230840 A | 7/2008 |
| CN | 101315556 A | 12/2008 |
| CN | 101315557 A | 12/2008 |
| CN | 101413521 A | 4/2009 |
| EP | 1 255 967 A1 | 11/2002 |
| KP | 10-2002-052433 | 7/2002 |
| TW | 0418373 B | 1/2001 |
| WO | WO-90/14640 A1 | 11/1990 |
| WO | WO-03/046511 A2 | 6/2003 |
| WO | WO-2008/154584 A1 | 12/2008 |

OTHER PUBLICATIONS

Increasing grid stability through accurate infeed forecasts of renewable energies Janek Zimmer; Armin Raabe; Tino Lemberg Integration of Renewables into the Distribution Grid, CIRED 2012 Workshop Year: 2012 pp. 1-4, DOI: 10.1049/cp.2012.0899 IET Conference Publications.*

Automated Calibration Method for Parallax Corrected Positioning Algorithms in Monolithic Scintillators Cedric Lemaitre; Peter Bruyndonckx; O. Devroede; M. Krieger; S. Tavernier; D. J. van der Laan; Marnix C. Maas; Denis R. Schaart 2006 IEEE Nuclear Science Symposium Conf., vol. 5 pp. 3135-3138, DOI: 10.1109/NSSMIC.2006.356539 IEEE.*

Demand side management verification system for electric vehicles M. Ferdowsi; A. Monti; F. Ponci; G. Fathi Applied Measurements for Power Systems Proceedings (AMPS), 2014 IEEE International Workshop on Year: 2014 pp. 1-6, DOI: 10.1109/AMPS.2014.6947724 IEEE Conference Publications.*

International Search Report and Written Opinion for Application No. PCT/MY2011/000039, dated Aug. 16, 2011.

International Preliminary Report on Patentability for Application No. PCT/MY201 1/000039, dated Oct. 5, 2012.

* cited by examiner

METHOD AND SYSTEM FOR VALIDATING ENERGY MEASUREMENT IN A HIGH PRESSURE GAS DISTRIBUTION NETWORK

FIELD OF INVENTION

The present invention broadly relates to a method and system for validating energy measurement in a high pressure gas distribution network.

BACKGROUND

Natural gas is a vital component of the world's supplies of energy. It is one of the cleanest, safest, and most useful energy sources. Natural gas is combustible, and when burned, it gives off a large amount of energy. However, unlike other fossil fuels, natural gas burns cleanly and emits lower levels of potentially harmful by-products into the air.

Typically, natural gas is a combustible mixture of hydrocarbon gases. While natural gas is formed primarily of methane, it can also include ethane, propane, butane and pentane. The composition of natural gas can vary widely. Once brought from underground, natural gas is refined to remove impurities like water, other gases, sand, and other compounds. Some hydrocarbons may be removed and sold separately, including propane and butane for liquefied petroleum gas (LPG) production. After refining, the clean natural gas is transmitted through a network of pipelines. From these pipelines, natural gas is delivered to its point of use.

Worldwide, natural gas is used for many residential, commercial, and industrial applications. Residential applications typically use natural gas for heating and cooling homes, heating water, and fuelling gas ranges. Commercial applications, such as grocery stores and office buildings, use natural gas for e.g. heating and cooling. For industrial applications, natural gas is used e.g. as a feedstock for making chemicals such as anhydrous ammonia, and as a fuel for boilers and furnaces which may, in turns, generate electricity.

As mentioned above, natural gas is supplied to the customers via natural gas pipelines. This requires metering stations to be placed periodically along specific sections of the natural gas pipelines. These stations allow pipeline companies to monitor and manage the natural gas in their pipes. Essentially, these metering stations measure the flow of gas along the pipeline and calculate the amount of energy from the natural gas that is being transported via underground pipelines to the respective customers, thereby allowing pipeline companies to 'track' the natural gas as it flows along the pipeline. These stations usually employ specialized meters and computers to measure the natural gas as it flows through the pipeline, without causing any flow interruptions to their respective customers. Such stations are also known as custody transfer points, where the ownership of gas molecules exchanges between contractual binding parties.

Accurate delivery to the customer is crucial for any natural gas transporter company. Any unaccounted for gas (UFG) can cause significant damage to the accounting book, i.e. a loss of profit. Typically, in order to manage the natural gas that enters the pipeline, and to ensure that all customers receive accurate delivery of their respective portions of this gas, sophisticated control systems are required to monitor the gas as it travels through all sections of the lengthy pipeline network.

For example, in a conventional approach, a supervisory control and data acquisition (SCADA) system is used. Billing is generated by the flow computer and the only means of verification is through validation, which is usually carried out e.g. once every 6 months. Thus, there may be errors in calculating the energy figure which are not timely detected. Some major contributing factors include drift, malfunctioning and freezing of measuring equipment (e.g. pressure, temperature and flow transmitters) at various custody transfer points, calculation error from the flow computer that is doing the billing calculation, gas chromatograph error and validation error. Importantly, a slight error in calculating the energy figure may lead to significant loss of profit.

A need therefore exists to provide a method and system for validating an energy measurement in a gas distribution network that seek to address at least one of the above problems.

SUMMARY

In accordance with a first aspect of the present invention, there is provided a method for validating energy measurement in a high pressure gas distribution network, the method comprising the steps of:

calculating a validation energy value using an artificial neural network (ANN) engine based on measured parameters associated with a gas flow in the gas distribution network;

measuring an actual energy value of the gas flow; and comparing the validation energy value and the actual energy value, wherein the actual energy value is validated if the validation energy value and the actual energy value are substantially equal.

The ANN engine may be programmed to represent an energy value prediction model based on the measured parameters.

The measured parameters may comprise a gross volume, a pressure, a temperature, a specific gravity and a calorific value of the gas flow.

The ANN engine may comprise a multilayered perceptron network structure.

The method may further comprise determining a percentage difference between the validation energy value and the measured energy value.

The method may further comprise identifying an alarm event based on the percentage difference exceeding a threshold.

The method may comprise providing the measured parameters as a block of data comprising respective sets of the measured parameters and respective measured energy values over a selected time period;

calculating respective validation energy values based on the respective sets of the measured parameters; and plotting both the measured energy values and the calculated validation energy values.

The method may further comprise learning the energy value prediction model.

The learning may comprise:

providing historical data for the measured parameters and the measured energy value; and applying a learning algorithm to the ANN engine based on the historical data.

Providing the historical data may comprise scaling the historical data for statistical standardization.

In accordance with a second aspect of the present invention, there is provided a system for validating energy measurement in a high pressure gas distribution network, comprising:

means for calculating a validation energy value using an artificial neural network (ANN) engine based on measured parameters associated with a gas flow in the gas distribution network;

means for measuring an actual energy value of the gas flow; and means for comparing the validation energy value and the actual energy value, wherein the actual energy value is validated if the validation energy value and the actual energy value are substantially equal.

The ANN engine may be programmed to represent an energy value prediction model based on the measured parameters.

The measured parameters may comprise a gross volume, a pressure, a temperature, a specific gravity and a calorific value of the gas flow.

The ANN engine may comprise a multilayered perceptron network structure.

The system may further comprise means for determining a percentage difference between validation energy value and the measured energy value.

The system may further comprise means for identifying an alarm event based on the percentage difference exceeding a threshold.

The system may comprise:

means for providing the measured parameters as a block of data comprising respective sets of the measured parameters and respective measured energy values over a selected time period;

means for calculating respective validation energy values based on the respective sets of the measured parameters; and means for plotting both the measured energy values and the calculated validation energy values.

The system may further comprise means for learning the energy value prediction model.

The means for learning may comprise:

means for providing historical data for the measured parameters and the measured energy value; and means for applying a learning algorithm to the ANN engine based on the historical data.

The means for providing the historical data may comprise means for scaling the historical data for statistical standardization In accordance with a third aspect of the present invention, there is provided a data storage medium comprising computer code means for instructing a computing device to execute a method for validating energy measurement in a high pressure gas distribution network, the method comprising the steps of:

calculating a validation energy value using an artificial neural network (ANN) engine based on measured parameters associated with a gas flow in the gas distribution network;

measuring an actual energy value of the gas flow; and comparing the validation energy value and the actual energy value, wherein the actual energy value is validated if the validation energy value and the actual energy value are substantially equal.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

The following example embodiments describe a method and system for validating energy measurement in a gas distribution network. Preferably, the method and system of the example embodiments can act as continuous validation as well as monitoring tools with regards to energy measurement.

Figure 1:
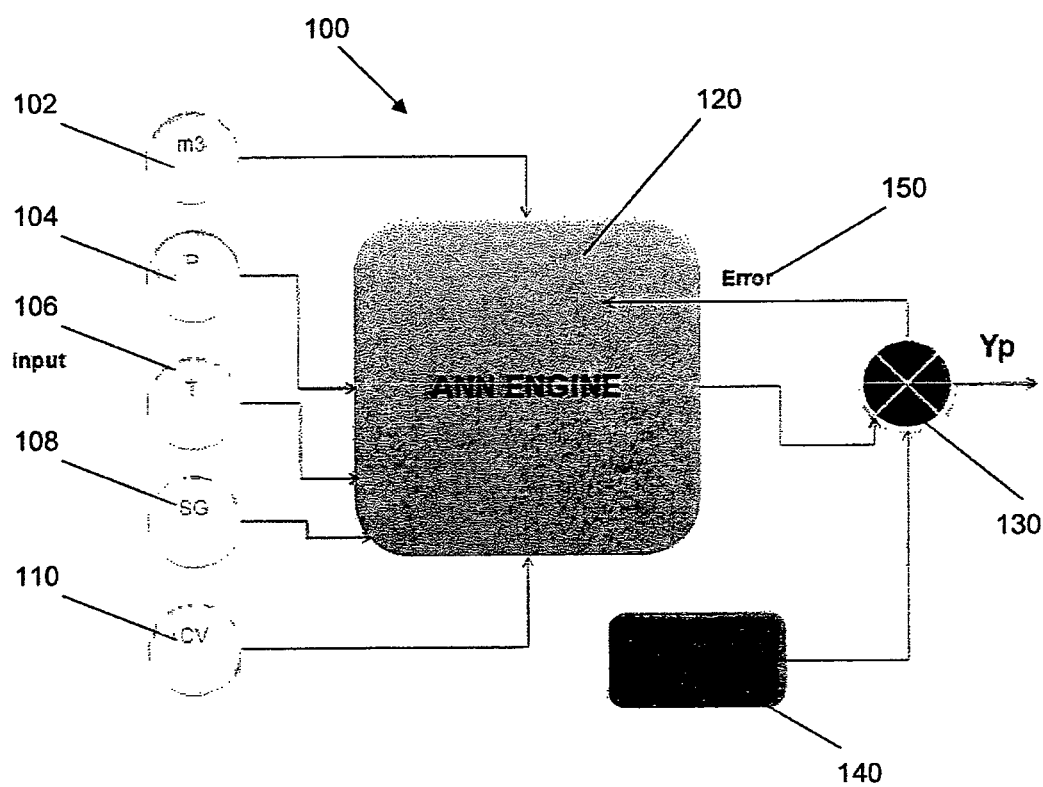
FIG. 1 shows a general block diagram of a system for validating an energy measurement in a gas distribution network according to an example embodiment.

FIG. 1 shows a general block diagram of a system 100 for validating energy measurement in a high pressure gas distribution network according to an example embodiment. System 100 comprises a prediction model engine 120 for predicting an energy value of the gas flow in the distribution network based on historical data of a plurality of parameters at that point. Preferably, the prediction model engine 120 comprises a trained artificial neural network (ANN) engine. In the example embodiment, the input parameters comprise gross volume 102, pressure 104, temperature 106, specific gravity 108 and calorific value 110 (to be discussed in detail below). The system 100 in this embodiment also comprises data storage means (not shown) and mechanism for retrieving and transmitting data to a control center, such as for example via a SCADA or a very small aperture terminal (V-SAT) system (not shown).

In the example embodiment, actual data of the input parameters is provided to the prediction model engine 120.

The predicted (i.e. validation) energy value 130 is compared with the measured energy value 140 obtained from field equipment (not shown) for determining an error/difference 150. Typically, under normal circumstances, a percentage error/difference between the predicted energy value 130 and the measured energy value 140 is less than about 1%, i.e. substantially equal. If, for any reason, any one of the input parameters is abnormal (e.g. a sudden spike or drop or drift), the predicted energy value 130 and the measured energy value 140 become substantially different as they are obtained from different methods in the example embodiment. Hence, in the example embodiment, the system 100 can advantageously identify potential billing errors. For example, if the error/difference 150 exceeds a predetermined threshold, the system can 100 alerts the user of the potential problems so that corrective actions may be taken. In addition, by employing an ANN engine, the system 100 of the example embodiment is advantageously capable of self learning in order to enhance the algorithm over time based on the collected historical data set.

Some portions of the description which follows are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "scanning", "calculating", "determining", "replacing", "generating", "initializing", "outputting", or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses apparatus for performing the operations of the methods. Such apparatus may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate. The structure of a conventional general purpose computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer effectively results in an apparatus that implements the steps of the preferred method.

Figure 2:
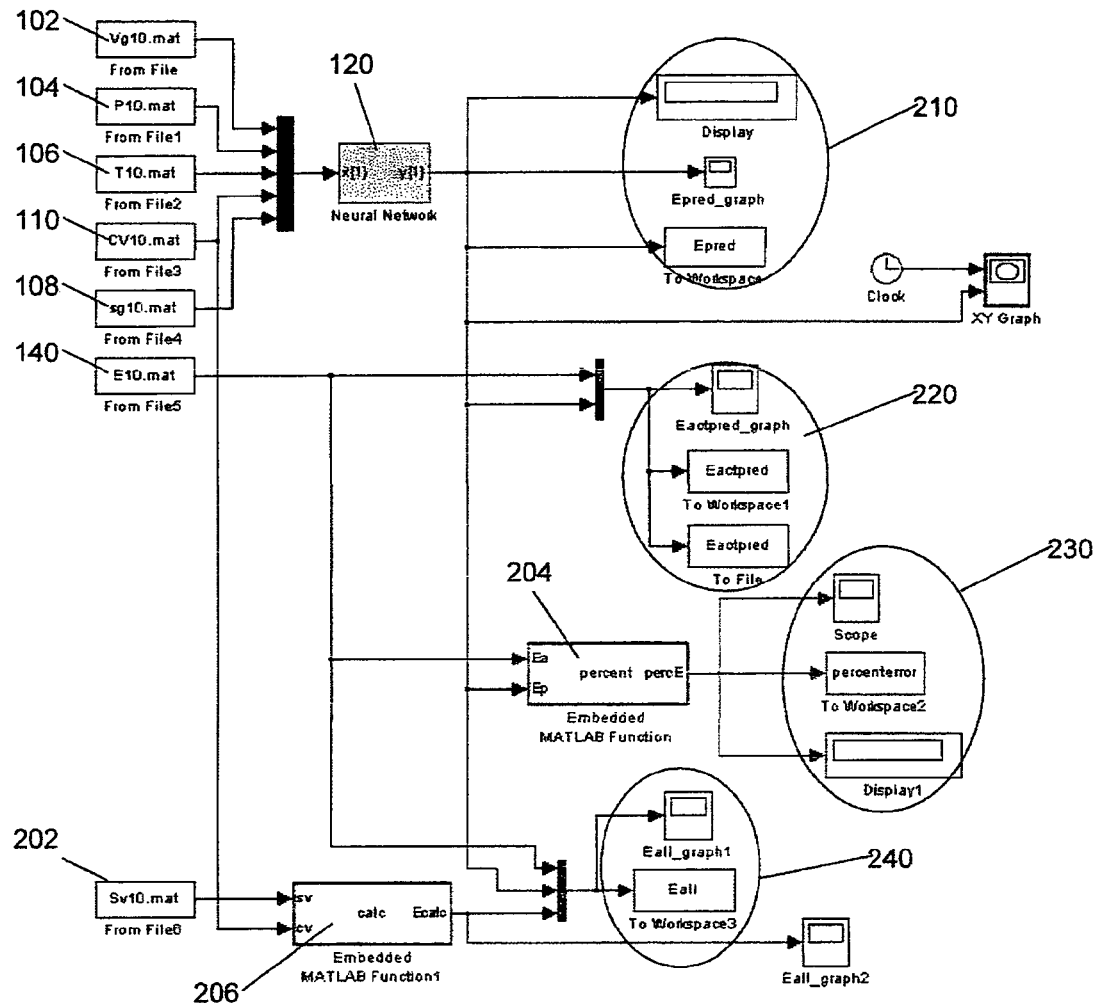
FIG. 2 shows a schematic diagram of an implementation of the system of FIG. 1 according to an example embodiment.

FIG. 2 shows a schematic diagram of an implementation of the system of FIG. 1 according to an example embodiment. The implementation is carried out in the example embodiment using MATLAB software from The MathWorks, Inc. However, it will be appreciated that other mathematical modeling software may be used in alternate embodiments.

As can be seen from FIG. 2, input parameters 102, 104, 106, 108, 110 corresponding to gross volume, pressure, temperature, specific gravity and calorific value respectively are provided to the prediction model engine 120. Additional input parameters to the system in the example embodiment include the actual (i.e. measured) energy value 140 and standard volume 202.

In the example embodiment, output 210 of the prediction model engine, in the form of the predicted energy value, is displayed as e.g. a graph or stored for further analysis. Preferably, output 210 is also used for calculating a difference 220 with the actual energy value 140, and for calculating a percentage error 230 when compared to the actual energy value 140 via a function 204. Furthermore, in this example embodiment, the calorific value 110 and standard volume 202 are optionally used to calculate an alternate energy value via a function 206. The alternate energy value can act as a further reference for verifying the predicted energy value. The predicted energy value, actual energy value and alternate energy value are then analyzed together and the output of the analysis is in the form of data 240.

Input Parameters

As described above, natural gas comprises primarily methane, but also significant quantities of ethane, butane, propane, carbon dioxide, nitrogen, helium, and hydrogen sulphide. Table 1 shows a typical composition of natural gas.

TABLE 1

| | | |
|---|---|---|
| Methane | $CH_4$ | 70-90% |
| Ethane | $C_2H_6$ | 0-20% |
| Propane | $C_3H_8$ | |
| Butane | $C_4H_{10}$ | |
| Carbon Dioxide | $CO_2$ | 0-8% |
| Oxygen | $O_2$ | 0-0.2% |
| Nitrogen | $N_2$ | 0-5% |
| Hydrogen Sulphide | $H_2S$ | 0-5% |
| Rare gases | A, He, Ne, Xe | trace |

In addition, the energy value is usually calculated based on the following equation:

Energy Value=Standard Volume(SV)×Calorific Value (CV)  (1)

where

Standard Volume(SV)=Gross Volume×Correction Factor(CF)  (2)

and $$CF = \frac{LineDensity}{BaseDensity}$$

or $$CF = \frac{P_L}{P_B} \times \frac{T_B}{T_L} \times \frac{Z_B}{Z_L}$$

where:

| | |
|---|---|
| $P_L$ = Line Pressure (bar a) | $Z_B$ = Base Compressibility factor |
| $P_B$ = Base Pressure (bar a) | $Z_L$ = Line Compressibility factor |
| $T_L$ = Line Temperature (K) | $T_B$ = Base Temperature (K) |

It will be appreciated that monitoring the energy value is preferred to just monitoring the flow rate as most major gas interconnects have some form of on-line energy measurement (in e.g. British Thermal Units or Btu). In addition, the methods for calculating the energy value of natural gas from analysis data are well documented in the art.

As can be seen from Equation (1), the energy value is proportional to the standard volume and calorific value of the gas being transported. The calorific value (or heating value) of natural gas is a measure of the heating power of the gas and typically depends on the composition of hydrocarbons in the gas. Impurities such as carbon dioxide, nitrogen, helium, hydrogen sulphide and other rare gases can influence the calorific value. Thus, the natural gas is preferably refined before being transported to remove the impurities, thereby improving the calorific value. In addition, in the example embodiment, a gas chromatograph is used to determine the gas composition for calculating the calorific value.

In addition, the compressibility factor (Z) typically relates to specific gravity of the gas, which is the density of the gas divided by the density of dry air of standard composition at the same specified conditions of pressure and temperature. By combining Equations (1) and (2), it can be seen that the energy value can be calculated based on gross volume, pressure, temperature, specific gravity and calorific value, which are used as input parameters in the example embodiment.

Prediction Model Engine

As described above, the prediction model engine 120 (FIG. 1) is built by training an artificial neural network (ANN) engine in the example embodiment. The general concept of ANN is understood by a person skilled in the art and can be summarized, for completeness, as follows.

Artificial neural network is inspired by the architecture of biological nervous system of human beings. Human nervous system contains a very large number (about 10 billion) of relatively simple nerve cells called neurons; each connected to about 10,000 other neurons. It functions in a parallel way to facilitate quick decisions. Electrochemical input signals, in the form of electrical spikes, are collected by a neuron from other neurons through a plurality of translucent structures called dendrites. Typically, the signal activity is sent out through an axon, which splits into thousands of branches. A synapse located at the end of each branch converts the activity from the axon into electrical effects that inhibit or excite activity in the connected neuron. If the excitatory input to the neuron is sufficiently large compared to inhibitory input, neuron sends an electrical spike activity to its axon. By adjusting the effectiveness of the synapses, the learning process can happen and the influence of one neuron on another may change as well.

Figure 3A:
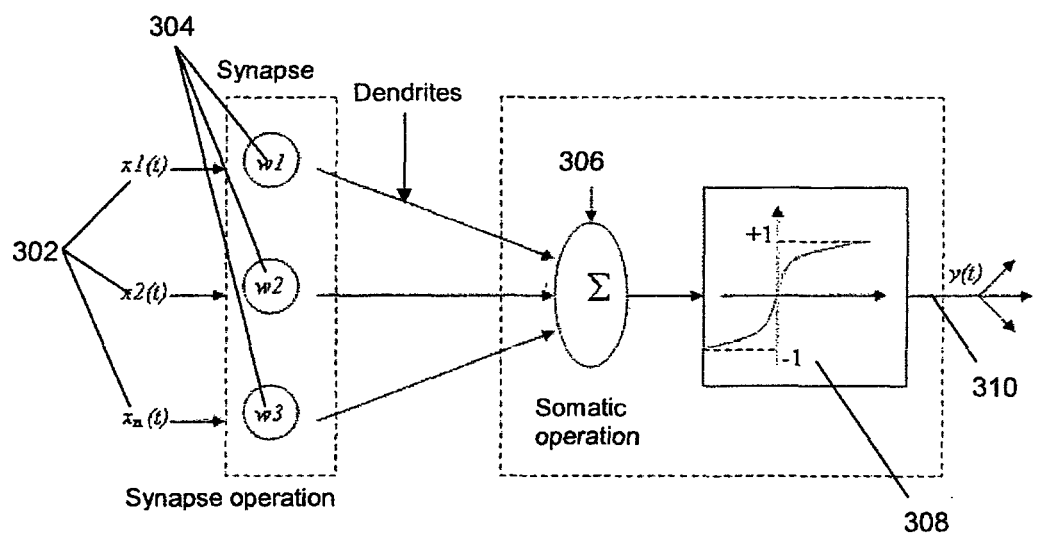
FIG. 3(a) shows a schematic representation of a perceptron.

FIG. 3(a) shows a schematic representation of a perceptron. The perceptron is a mathematical model of a biological neuron. Similar to a neuron, the electrical signals received by dendrites from the axons of other neurons are represented as numerical values in the perceptron. The electrical signals are modulated in various amounts at the synapses between the dendrite and axons. As can be seen from FIG. 3(a), in the perceptron, the signals are represented by multiplying each input value 302 by a value called the weight 304. Typically, when the total strength of the input signals is above a certain threshold value, a neuron excites an output signal. This event is represented in a perceptron by determining, at a summing junction 306, a weighted sum of the all inputs, which corresponds to a total strength of the input signals. Then, the sum is applied to an activation function 308 for limiting the amplitude of an output 310 to a permissible finite value within an output range.

Figure 3B:
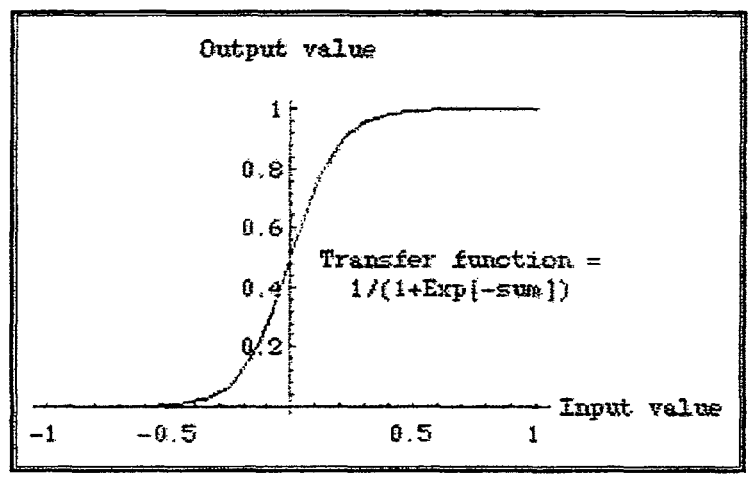
FIG. 3(b) shows a graph of an activation function used in the system of an example embodiment.

FIG. 3(b) shows a graph of an activation function 310 used in the artificial neural network engine of an example embodiment. The activation function is denoted by a function φ(v) that defines the output of neuron of induced local field v. In the example embodiment, the activation function is a sigmoid function. As can be seen in FIG. 3(b), the graph of the sigmoid function comprises an S-shape which defines a strictly increasing function that results in a balance of linear and nonlinear behavior. The expression of the function is as follows:

$$\varphi(v) = \frac{1}{1 + \exp(-av)} \qquad (3)$$

$$v_j^1(t) = F(s_j(t)) \qquad (4)$$

where a is a slope value of sigmoid function. As a varies, the sigmoid function slope varies as well. The function is continuous between +1 to −1.

Figure 4:
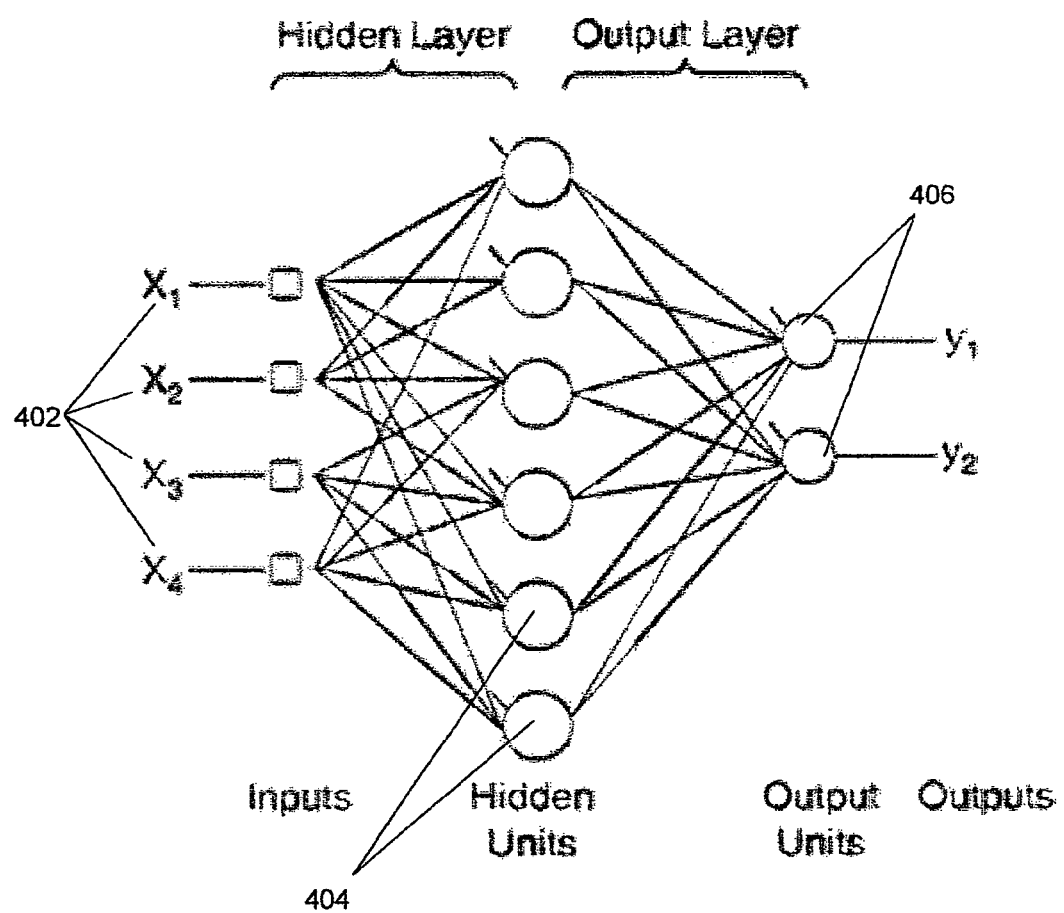
FIG. 4 shows a schematic representation of a multilayered perceptron (MLP) network according to an example embodiment.

In addition, in the example embodiment, a multilayered perceptron (MLP) network is used for modeling the neural network architecture. FIG. 4 shows a schematic representation of the MLP network of the example embodiment. The inputs 402 of the network act as sources for hidden layer and output layer in the example embodiment. The hidden layer nodes 404 are also fed as inputs for output layer nodes 406 and the output layer gives out the overall response of the network.

For example, for a MLP network with $n_i$ inputs, $n_h$ hidden nodes and $n_o$ outputs, the expression for $\hat{y}_k(t)$, the output of the $k^{th}$ neuron in the output layer is given by:

$$\hat{y}_k(t) = \sum_{j=1}^{n_h} w_{jk}^2 v_j^1(t) \qquad (5)$$

where k=1, 2, . . . , $n_o$; j=1, 2, $n_h$; and i=1, 2, . . . , $n_i$ for each discrete time t, and $w_{jk}^2$ denote the respective weights.

Also, in Equation (5), the superscripts indicate the layer number, i.e. 0, 1 and 2 denote input, hidden and output layers respectively. The additional applied input, bias ($b_k^2$ and $b_j^1$) has an effect of increasing or decreasing the net input of the activation function depending on whether it is positive or negative value respectively. The overall expression for MLP derived from Equations (4) and (5) is given by:

$$\hat{y}_k(t) = \sum_{j=1}^{n_h} w_{jk}^2 F\left(\sum_{i=1}^{n_i} w_{ij}^1 v_i^0(t) + b_j^1\right) \quad (6)$$

Typically, the values of the weights are unknown and for selected values should preferably minimize the error of prediction. Hence, the sigmoid function expression is as follows:

$$F(x) = \frac{1}{1 + \exp(-x)} \quad (7)$$

The purpose of training algorithm is to determine the values of $w_{ij}^1$ and $w_{jk}^2$ as shown in Equation (6). The definition of learning, as will be appreciated by a person skilled in the art, implies the sequence of events where the neural network is stimulated by an environment. As the result of stimulation, a neural network experience changes in its free parameters. Due to the existence of the changes in the structure internally, the neural network reacts to adjust itself to the new environment. In the example embodiment, based on error correction learning, the output signal of the network is compared to the desired response or target value, denoted by $d_k(n)$. Therefore, error signal expression becomes:

$$e_k(n) = d_k(n) - \hat{y}_k(n) \quad (8)$$

where $e_k(n)$ is an error signal that preferably triggers a control mechanism in order to correct the synaptic weight parameters. This corrective adjustment method advantageously allows the network output to be achieved as close as possible to a target response, thereby reducing the error.

Typically, back propagation (BP) algorithm is used to find optimum values for the above parameters. Although the algorithm can be implemented easily and produces a good performance, its convergence rate is slow. To overcome the problems, a recursive prediction error (RPE) algorithm is used in the example embodiment to replace the BP algorithm. The RPE algorithm preferably provides a better performance, e.g. a faster convergence rate and better final convergence values of weights and thresholds. It will be appreciated by a person skilled in the art that RPE algorithm is a Gauss-Newton type algorithm and has been used to train MLP networks.

In the example embodiment, the RPE algorithm is implemented to minimize a cost function as defined by Equation (9):

$$J(\hat{\Theta}) = \frac{1}{2N} \sum_{t=1}^{N} \varepsilon^T(t, \hat{\Theta}) \Lambda^{-1} \varepsilon(t, \hat{\Theta}) \quad (9)$$

where $\epsilon(t)$ and $\Lambda$ are the prediction error and m×m symmetric positive definite matrix respectively. The minimization of the cost function is achieved in the example embodiment by recursively updating the estimated parameter vector $\hat{\Theta}$ using a Gauss-Newton algorithm as follows:

$$\hat{\Theta}(t) = \hat{\Theta}(t-1) + P(t)\Delta(t) \quad (10)$$

and $$\Delta(t) = \alpha_m(t)\Delta(t-1) + \alpha_g(t)\psi(t)\epsilon(t) \quad (11)$$

where $\alpha_m(t)$ and $\alpha_g(t)$ are the momentum and learning rate respectively. The values for $\alpha_m(t)$ and $\alpha_g(t)$ can be assigned randomly in range between 0 and 1. Typically, $\alpha_m(t)$ has a value closer to 1 and $\alpha_g(t)$ has a value closer to 0. Also, $\psi(t)$ is a gradient of the one-step ahead predicted output with respect to the network parameters and the expression is given by in Equation (12):

$$\psi(t, \Theta) = \left[\frac{d\hat{y}(t, \Theta)}{d\Theta}\right] \quad (12)$$

In addition, the values for P(t) (Equation (10)) is updated recursively by the following equation:

$$P(t) = \frac{1}{\lambda(t)}\left[P(t-1) - P(t-1)\psi(t)\right. \quad (13)$$
$$\left.(\lambda(t)I + \psi^T(t)P(t-1)\psi(t))^{-1}\psi^T(t)P(t-1)\right]$$

where $\lambda(t)$ is the forgetting factor and has a value within 0 to 1, and is usually updated using the following scheme:

$$\lambda(t) = \lambda_o \lambda(t-1) + (1-\lambda_o) \quad (14)$$

In the example embodiment, the initial value for the P(t) matrix is P(0) and is set to a value of αI where I is the identity matrix and α is a constant having a typical value between 100 and 10000. It will be appreciated that a very small value of a can cause slow learning. On the other hand, a very large value of α may cause the estimated parameter to fail to converge properly. Thus, the selected α value advantageously is between 100 and 10000. Preferably, α is taken to be 1000.

It will be appreciated that, in order to obtain an optimized model of neural network, the number of hidden nodes, momentum and learning rate must be established first. In the example embodiment, the model is trained using several hidden nodes, momentum and learning rates. Preferably, the optimum parameter values are selected and saved if the trained model gives a minimum error of energy prediction performance. Once the optimized model is derived, the ANN is directly used for validation.

In the example embodiment, the ANN model is trained based on data obtained, e.g. on hourly basis, from the flow computer of a gas metering station. From the given data, two sets are divided for training and testing purposes. For example, 16% of the overall data is randomly selected for testing (also called validation) and the rest is allocated as training data. Initially, the data is scaled to get statistically standardized in order to meet a predefined range with respect to all values of data. The standardized data is then applied to the prediction model engine.

For example, the optimum learning rate $\alpha_g(t)$ and momentum $\alpha_m(t)$ have been found to be 0.1 and 0.8 respectively for a minimum Mean Absolute Error (MAE) at $5.174 \times 10^{-2}$ in the example embodiment. In addition, the number of hidden nodes corresponding to the minimum MAE is 4 in an example embodiment.

Figure 5A:
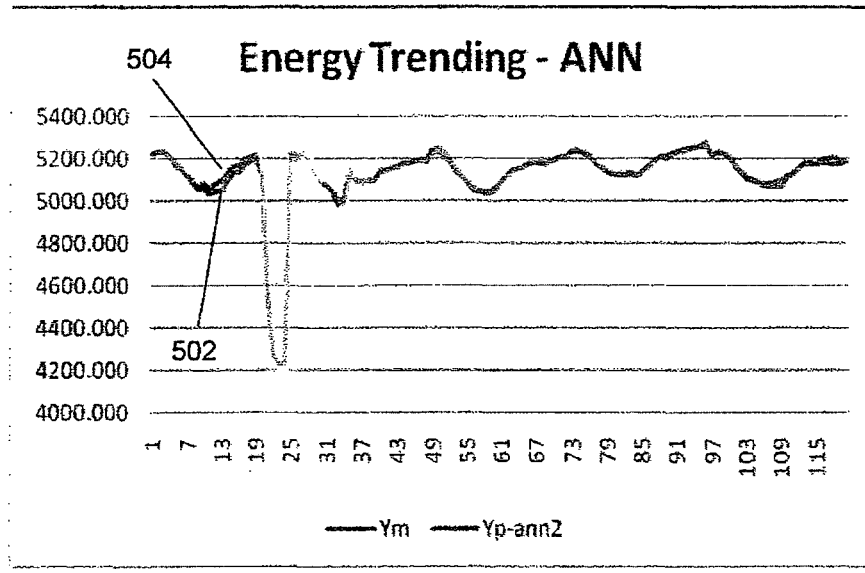
FIG. 5(a) shows a graph comparing the energy value predicted using an artificial neural network (ANN) engine and the measured energy value in an example embodiment.
Figure 5B:
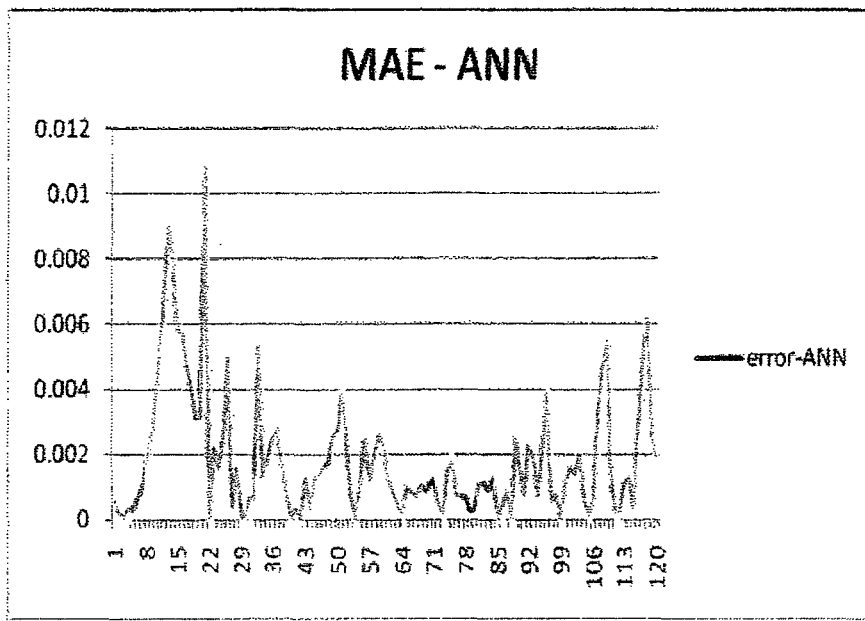
FIG. 5(b) shows a graph illustrating the Mean Absolute Error (MAE) performance of the ANN engine of the example embodiment.

FIG. 5(a) shows a graph comparing the energy value predicted using an ANN engine and the measured energy value in an example embodiment. FIG. 5(b) shows a graph illustrating the MAE performance of the ANN engine of the example embodiment. Preferably, the graphs of FIGS. 5(a)-(b) are obtained based on randomly selected testing data. It can be seen from FIG. 5(a) that the predicted energy value 502 generated by ANN engine is substantially the same as the measured energy value 504 from the test data, even when there is a significant fluctuation in the energy value. This is confirmed by the MAE values in FIG. 5(b) where the maximum MAE is only about 0.0108, i.e. the ANN model of the example embodiment is advantageously robust.

Figure 5C:
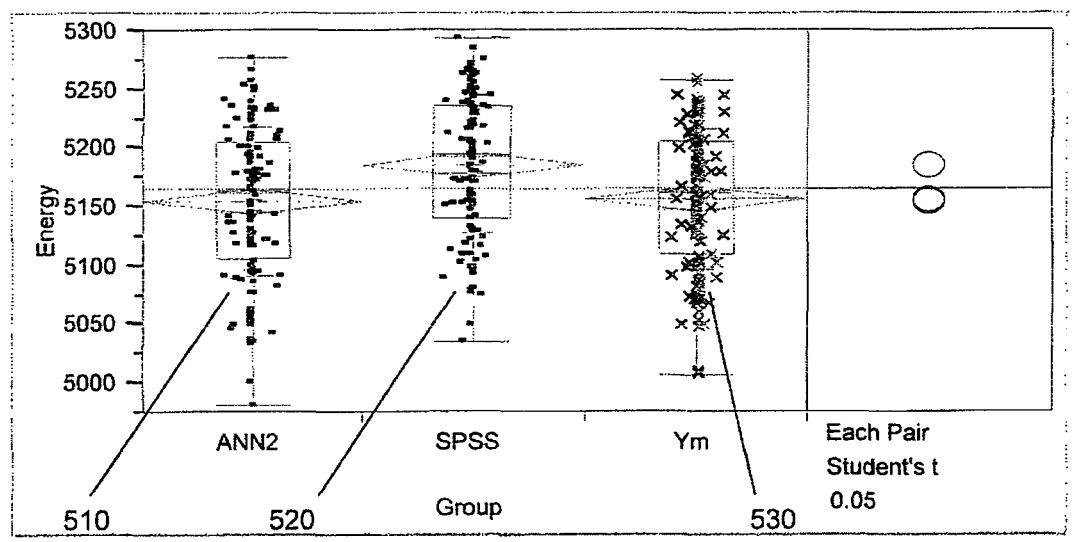
FIG. 5(c) shows a chart comparing the performance of the ANN engine of the example embodiment with that of a conventional regression method.

FIG. 5(c) shows a chart comparing the performance of the ANN engine of the example embodiment with that of a conventional regression method. As can be seen from FIG. 5(c), in terms of both mean value (using e.g. a standard analysis of variance (ANOVA) test) and distribution of overall data, results 510 based on the ANN engine of the example embodiment are substantially similar to the measured energy values 530, while results 520 based on the conventional regression method show a significant difference. In other words, the ANN engine in the example embodiment can accurately model the measured energy values.

Figure 6:
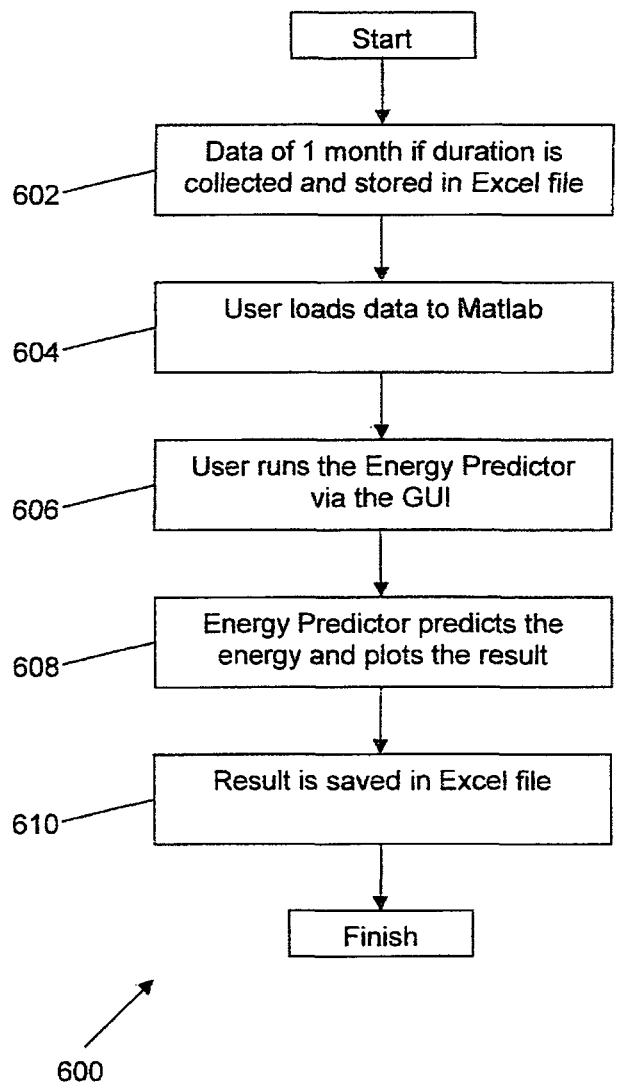
FIG. 6 shows a flow chart illustrating a method of operating the validating system according to an example embodiment.

FIG. 6 shows a flow chart 600 illustrating a method of operating the monitoring system according to an example embodiment. At step 602, historical data of e.g. 1 month duration is collected and stored in e.g. an Excel file. At step 604, the data is loaded to the system using e.g. MATLAB. At step 606, the energy prediction model engine is run via the graphical user interface (GUI) of the system. At step 608, the energy value is predicted and the result is plotted, e.g. against the actual energy value and/or as a percentage error graph. At step 610, the result is saved in e.g. an Excel file for archive purposes.

Figure 7:
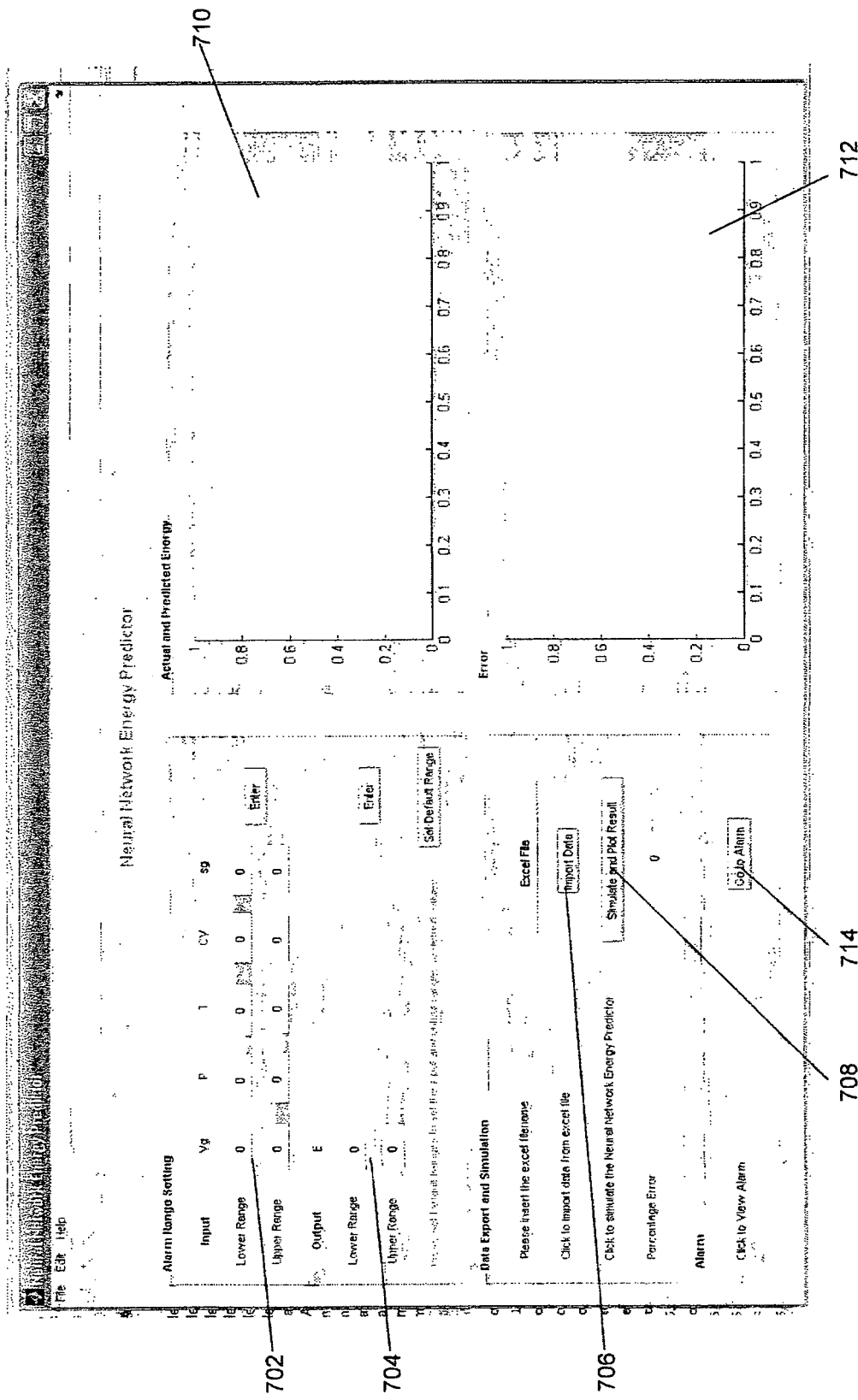
FIG. 7 shows a screen-shot of the graphical user interface (GUI) of the monitoring system according to an example embodiment.

FIG. 7 shows a screen-shot of the GUI of the system according to an example embodiment. The GUI comprises boxes 702 for setting an input range, e.g. a lower and an upper value, of the input parameters. Similarly, boxes 704 are provided for setting an output range of the output energy value, e.g. a lower and an upper value. In the example embodiment, the setting of the input and output ranges advantageously reduces or minimizes the risk of feeding the system with invalid data. This preferably acts as a first filtration mechanism before feeding the data for energy prediction. The system will trigger an alarm if any of the ranges is being exceeded. The GUI also provides input means 706 for importing the historical data from e.g. an Excel file. Once the data is available, the prediction model engine is run in the example embodiment by pressing a "Simulate" button 708. The GUI further comprises at least a graph 710 of the actual and predicted energy values and a percentage error graph 712, for easy reference.

Any alarm raised by the system is viewed in the example embodiment by pressing an "Alarm" button 714. For example, the "Alarm" button 714 enables the user to see if there is any abnormality in the input/output ranges, drifting of data, or if the difference between the predicted energy value and the actual energy value is more than 1%. In a preferred embodiment, the "Alarm" button 714 is replaced by an automatic alarm triggering mechanism, i.e. the alarm message is automatically presented without the user having to press a button.

Figure 8A:
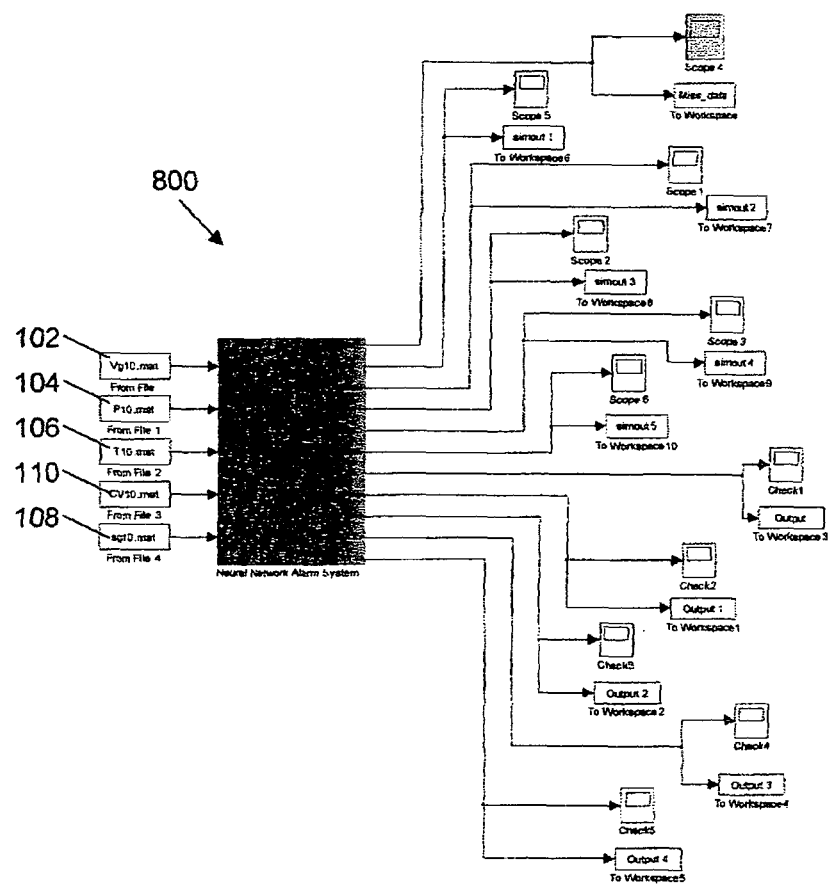
FIG. 8(a) shows a general schematic diagram illustrating an alarm system according to an example embodiment.
Figure 8B:
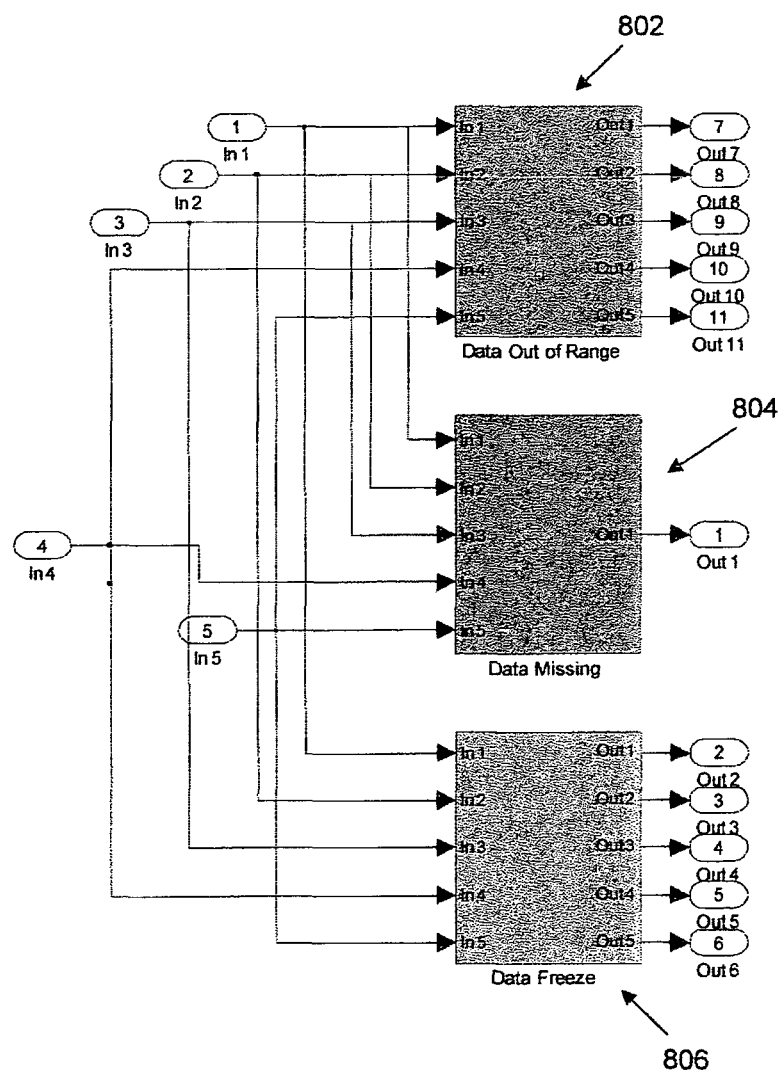
FIG. 8(b) shows a detailed schematic diagram of an implementation of the alarm system of FIG. 8(a).
Figure 8C:
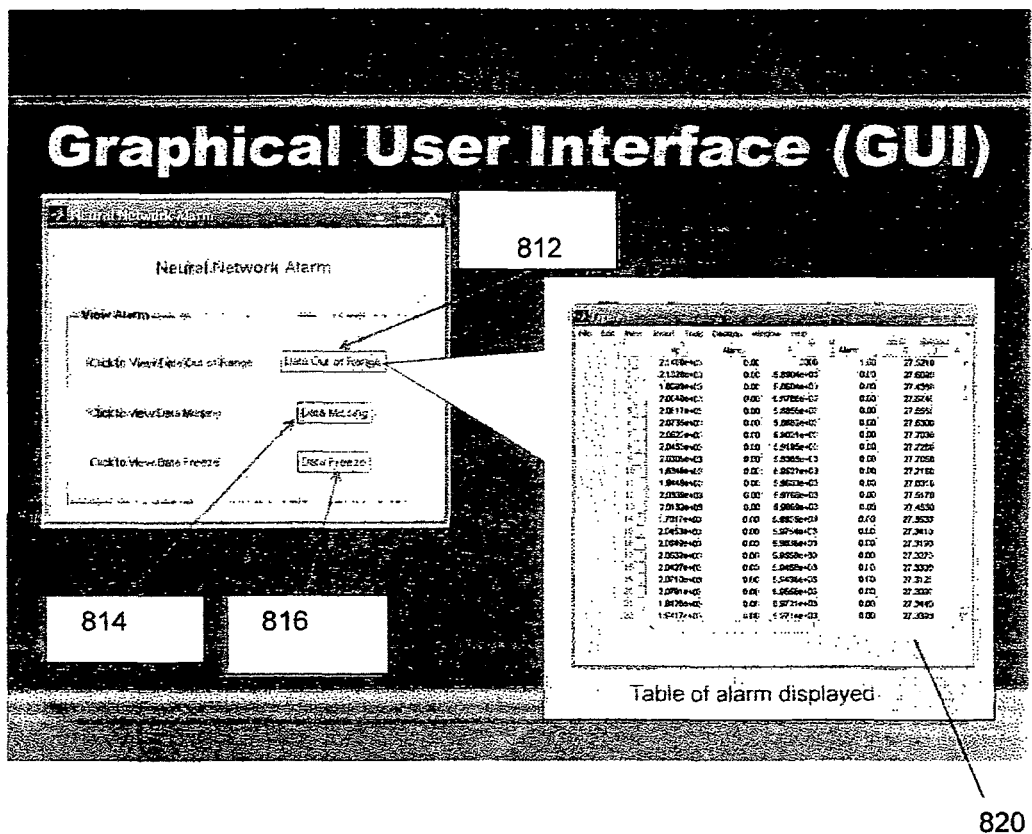
FIG. 8(c) shows a screen-shot of the GUI of the alarm system according to an example embodiment.

FIG. 8(a) shows a general schematic diagram illustrating an alarm system 800 according to an example embodiment. FIG. 8(b) shows a detailed schematic diagram of an implementation of the alarm system 800 of FIG. 8(a). FIG. 8(c) shows a screen-shot of the GUI of the alarm system according to an example embodiment.

As can be seen from FIG. 8(a), the inputs In1-In5 of the alarm systems correspond to the gross volume 102, pressure 104, temperature 108, calorific value 110 and specific gravity 108 (FIG. 1) respectively.

In FIG. 8(b), three example alarm functions, i.e. Data Out Of Range, Data Missing and Data Freeze, are implemented by blocks 802, 804 and 806 respectively. It will be appreciated that the alarm system 800 of the example embodiment is not limited to the above alarm functions, and additional alarm functions may be configured.

In FIG. 8(c), the three alarm functions of FIG. 8(b) are implemented via buttons 812, 814 and 816 respectively. By clicking a button, the respective alarm is displayed, e.g. in a table or graph in an Excel file. An example table of alarms is shown in FIG. 8(c) as a pop-up window 820.

Figure 9:
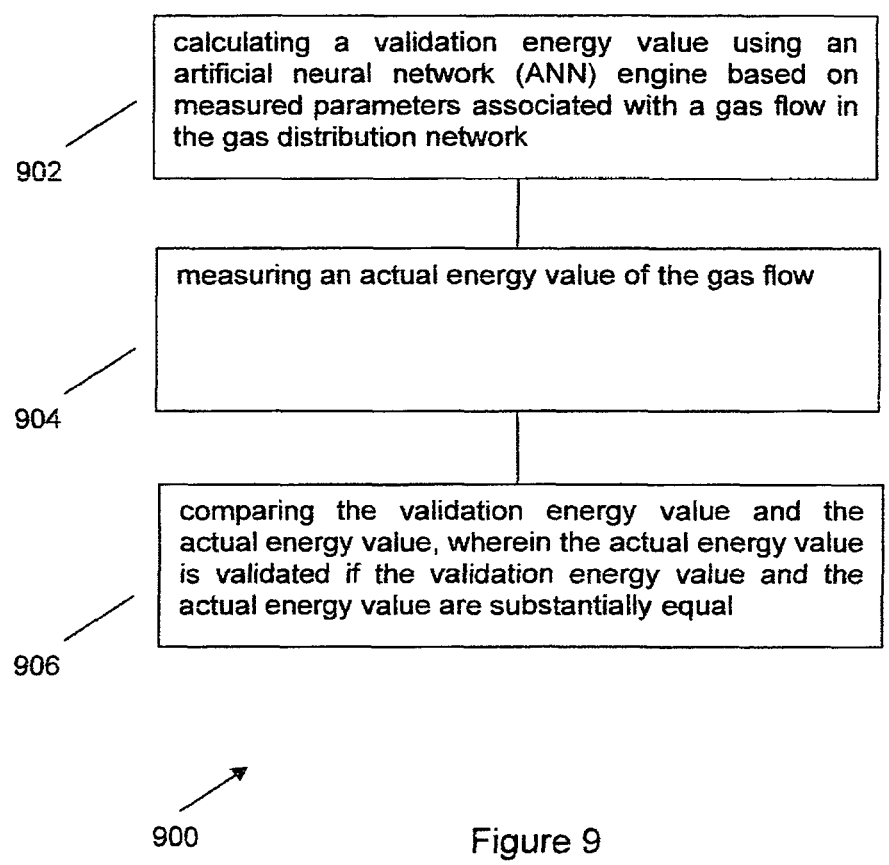
FIG. 9 shows a flow chart illustrating a method for validating an energy measurement in a gas distribution network according to an example embodiment.

FIG. 9 shows a flow chart 900 illustrating a method for validating energy measurement in a high pressure gas distribution network according to an example embodiment. At step 902, a validation energy value is calculated using an artificial neural network (ANN) engine based on measured parameters associated with a gas flow in the gas distribution network. At step 904, an actual energy value of the gas flow is measured. At step 906, the validation energy value and the actual energy value are compared, wherein the actual energy value is validated if the validation energy value and the actual energy value are substantially equal.

Figure 10:
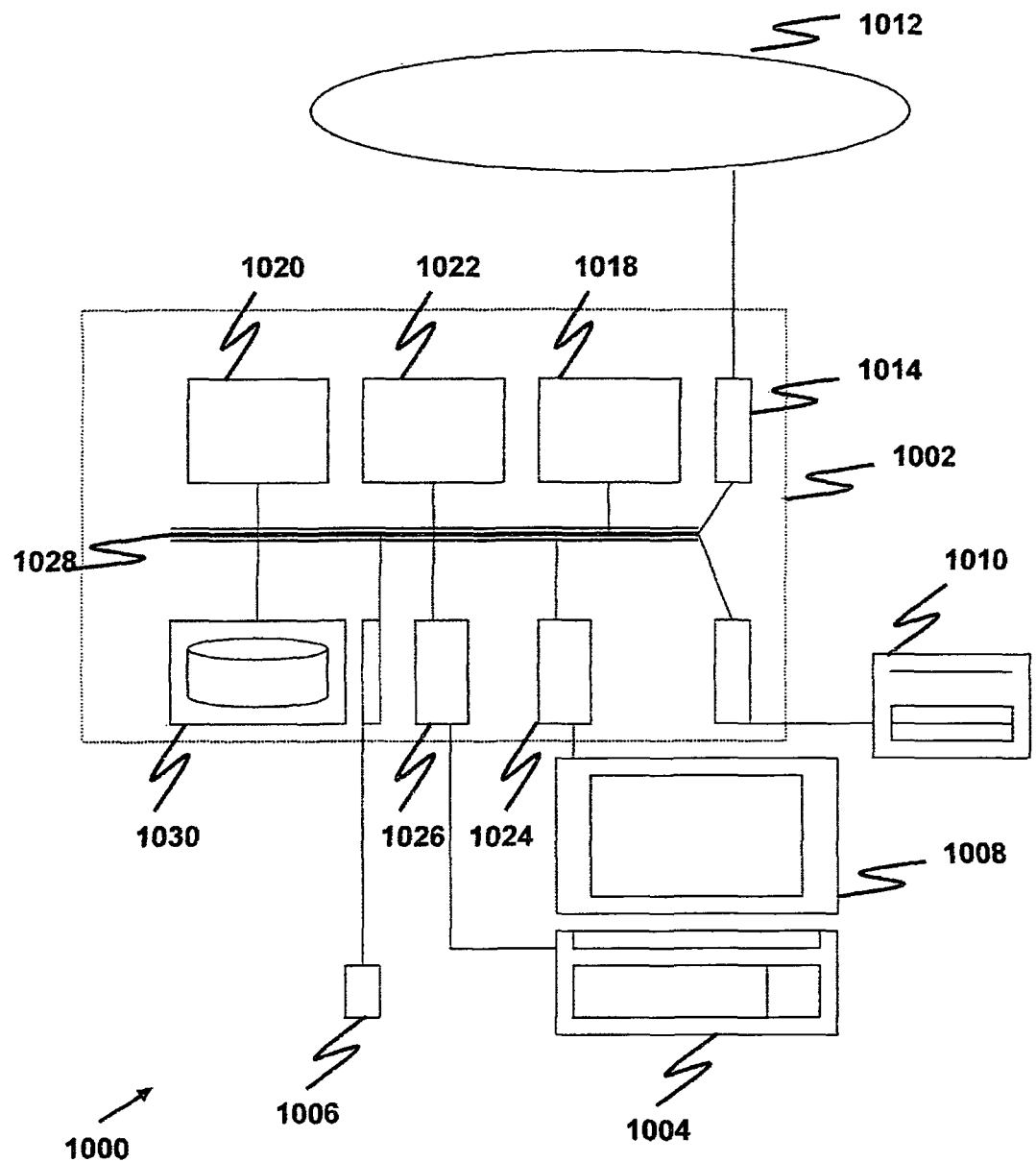
FIG. 10 shows a general block diagram of a computer system for implementing the method and system of an example embodiment.

The method and system of the example embodiment can be implemented on a computer system 1000, schematically shown in FIG. 10. It may be implemented as software, such as a computer program being executed within the computer system 1000, and instructing the computer system 1000 to conduct the method of the example embodiment.

The computer system 1000 comprises a computer module 1002, input modules such as a keyboard 1004 and mouse 1006 and a plurality of output devices such as a display 1008, and printer 1010.

The computer module 1002 is connected to a computer network 1012 via a suitable transceiver device 1014, to enable access to e.g. the Internet or other network systems such as Local Area Network (LAN) or Wide Area Network (WAN).

The computer module 1002 in the example includes a processor 1018, a Random Access Memory (RAM) 1020 and a Read Only Memory (ROM) 1022. The computer module 1002 also includes a number of Input/Output (I/O) interfaces, for example I/O interface 1024 to the display 1008, and I/O interface 1026 to the keyboard 1004.

The components of the computer module 1002 typically communicate via an interconnected bus 1028 and in a manner known to the person skilled in the relevant art.

The application program is typically supplied to the user of the computer system 1000 encoded on a data storage medium such as a CD-ROM or flash memory carrier and read utilizing a corresponding data storage medium drive of a data storage device 1030. The application program is read and controlled in its execution by the processor 1018. Intermediate storage of program data maybe accomplished using RAM 1020.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. A method for validating energy measurement in a high pressure gas distribution network, the method comprising the steps of:
   calculating a validation energy value using an artificial neural network (ANN) engine based on measured parameters associated with a gas flow in the gas distribution network;
   measuring a field energy value of the gas flow; and
   comparing the validation energy value and the measured energy value, wherein the measured energy value is validated if the validation energy value and the measured energy value are substantially equal.

2. The method as claimed in claim 1, wherein the ANN engine is programmed to represent an energy value prediction model based on the measured parameters.

3. The method as claimed in claim 1, wherein the measured parameters comprise a gross volume, a pressure, a temperature, a specific gravity, and a calorific value of the gas flow.

4. The method as claimed in claim 1, wherein the ANN engine comprises a multilayered perceptron network structure.

5. The method as claimed in claim 1, further comprising determining a percentage difference between the validation energy value and the measured energy value.

6. The method as claimed in claim 5, further comprising identifying an alarm event based on the percentage difference exceeding a threshold.

7. The method as claimed in claim 1, comprising providing the measured parameters as a block of data comprising respective sets of the measured parameters and respective measured energy values over a selected time period;
   calculating respective validation energy values based on the respective sets of the measured parameters; and
   plotting both the measured energy values and the calculated validation energy values.

8. The method as claimed in claim 1, further comprising learning the energy value prediction model.

9. The method as claimed in claim 8, wherein the learning comprises:
   providing historical data for the measured parameters and the measured energy value; and
   applying a learning algorithm to the ANN engine based on the historical data.

10. The method as claimed in claim 9, wherein providing the historical data comprises scaling the historical data for statistical standardization.

11. A system for validating energy measurement in a high pressure gas distribution network, comprising:
    means for calculating a validation energy value using an artificial neural network (ANN) engine based on measured parameters associated with a gas flow in the gas distribution network;
    means for measuring a field energy value of the gas flow; and
    means for comparing the validation energy value and the measured energy value, wherein the measured energy value is validated if the validation energy value and the measured energy value are substantially equal.

12. The system as claimed in claim 11, wherein the ANN engine is programmed to represent an energy value prediction model based on the measured parameters.

13. The system as claimed in claim 11, wherein the measured parameters comprise a gross volume, a pressure, a temperature, a specific gravity, and a calorific value of the gas flow.

14. The system as claimed in claim 11, wherein the ANN engine comprises a multilayered perceptron network structure.

15. The system as claimed in claim 11, further comprising means for determining a percentage difference between validation energy value and the measured energy value.

16. The system as claimed in claim 15, further comprising means for identifying an alarm event based on the percentage difference exceeding a threshold.

17. The system as claimed in claim 11, comprising:
    means for providing the measured parameters as a block of data comprising respective sets of the measured parameters and respective measured energy values over a selected time period;
    means for calculating respective validation energy values based on the respective sets of the measured parameters; and
    means for plotting both the measured energy values and the calculated validation energy values.

18. The system as claimed in claim 11, further comprising means for learning the energy value prediction model.

19. The system as claimed in claim 18, wherein the means for learning comprises:
    means for providing historical data for the measured parameters and the measured energy value; and
    means for applying a learning algorithm to the ANN engine based on the historical data.

20. The system as claimed in claim 19, wherein means for providing the historical data comprises means for scaling the historical data for statistical standardization.

21. A data storage medium comprising computer code for instructing a computing device to execute a method for validating energy measurement in a high pressure gas distribution network, the method comprising the steps of:
    calculating a validation energy value using an artificial neural network (ANN) engine based on measured parameters associated with a gas flow in the gas distribution network;
    measuring a field energy value of the gas flow; and
    comparing the validation energy value and the measured energy value, wherein the measured energy value is validated if the validation energy value and the measured energy value are substantially equal.

* * * * *